(12) United States Patent
Ota et al.

(10) Patent No.: US 7,087,669 B2
(45) Date of Patent: Aug. 8, 2006

(54) ABSORBENTS AND PROCESS FOR PRODUCING THE SAME, ABSORBABLE CONSTRUCTS AND ABSORBABLE ARTICLES

(75) Inventors: Yoshihisa Ota, Kyoto (JP); Yoshiyuki Iwasaki, Kyoto (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 298 days.

(21) Appl. No.: 10/333,420

(22) PCT Filed: Jul. 13, 2001

(86) PCT No.: PCT/JP01/06111

§ 371 (c)(1),
(2), (4) Date: Jul. 7, 2003

(87) PCT Pub. No.: WO02/05949

PCT Pub. Date: Jan. 24, 2002

(65) Prior Publication Data

US 2004/0024104 A1    Feb. 5, 2004

(30) Foreign Application Priority Data

Jul. 18, 2000    (JP)    ............................. 2000-216785

(51) Int. Cl.
*C08K 3/34*    (2006.01)
(52) U.S. Cl. ...................... 524/493; 524/492; 524/556; 525/329.7; 428/500; 428/913
(58) Field of Classification Search ................ 524/492, 524/493, 556; 525/329.7; 428/500, 913
See application file for complete search history.

(56) References Cited

U.S. PATENT DOCUMENTS

| | | | |
|---|---|---|---|
| 3,932,322 A * | 1/1976 | Duchane | 524/430 |
| 5,002,986 A * | 3/1991 | Fujiura et al. | 524/47 |
| 5,087,656 A | 2/1992 | Yoshinaga et al. | 524/493 |
| 5,147,921 A | 9/1992 | Mallo | 524/493 |
| 5,258,448 A * | 11/1993 | Mallo et al. | 524/556 |
| 5,489,469 A * | 2/1996 | Kobayashi et al. | 442/393 |
| 5,849,816 A * | 12/1998 | Suskind et al. | 523/201 |
| 6,288,158 B1 | 9/2001 | Schapowalov et al. | 524/493 |

FOREIGN PATENT DOCUMENTS

| | | |
|---|---|---|
| EP | 0 844 270 | 5/1998 |
| JP | 56-133028 | 10/1981 |
| JP | 63-267435 | 11/1988 |
| JP | 7-88171 | 4/1995 |
| JP | 8-47637 | 2/1996 |
| JP | 11-93073 | 4/1999 |
| JP | 11-315112 | 11/1999 |

OTHER PUBLICATIONS

"Polymerization of Methyl Methacrylate with the Carbon Tetrachloride/Dichlorotris-(triphenylphosphine) ruthenium (II)/Methylaluminum Bis (2,6-di-tert-butylphenoxide) Initiating System: Possibility of Living Radical Polymerization", Mitsuru Kato et al., 1995 American Chemical Society.

* cited by examiner

*Primary Examiner*—Helen L. Pezzuto
(74) *Attorney, Agent, or Firm*—Baker & Daniels (57) ABSTRACT

Absorbents comprising an water-absorbable resin and water-insoluble nonporous spherical monoparticles having an average diameter of 1 to 50 nm; a process for producing these absorbent by mixing the spherical monoparticles, which have been solubilized in water, with dry powdery particles of the water-absorbable resin; absorbable constructs composed of the above absorbent with a matrix wherein the amount of the absorbent ranges from 30 to 95% by weight based on the absorbable construct; and absorbable articles provided with the absorbable construct, a liquid-permeable sheet and an air-permeable back sheet. These absorbents, absorbable constructs and absorbable articles are excellent in the diffusion/absorption speed and absorption amount of a liquid within the resin even in case of absorbing a liquid containing water-insoluble or hardly water-soluble matters such as menstrual blood or feces.

17 Claims, 1 Drawing Sheet

FIG.1

ABSORBENTS AND PROCESS FOR PRODUCING THE SAME, ABSORBABLE CONSTRUCTS AND ABSORBABLE ARTICLES

TECHNICAL FIELD

The present invention relates to absorbents and a process for producing the same, absorbable constructs and absorbable articles. More specifically, the present invention relates to absorbents and a process for producing the same, absorbable constructs and absorbable articles, all of which have an excellent diffusion/absorption speed and an absorption amount of the liquid absorbed within an absorbable resin even in case the liquid to be absorbed contains water-insoluble or hardly water-soluble matters such as menstrual blood or feces.

BACKGROUND ART

Up to now, various methods have been proposed for improving the absorption speed of water-absorbable resins which are used as absorbents for a paper diaper and the like, some of them as described below are based on a concept of increasing the area contacting with a liquid to be absorbed by broadening the surface area of the water-absorbable resins.
a. A method of rendering a water-absorbable resin porous by adding a low-boiling point volatile solvent to a polymerization solution to be used in the manufacturing process of the water-absorbable resin, and vaporizing the volatile solvent with polymerization heat (Japanese Patent Application Laid-Open No.S59-18712 (1984));
b. A method of forming a foam type resin by blending a carboxyl group-containing water-absorbable resin and glycidyl group-containing polyolefin resin with a crosslinking agent and pyrolytic foaming agent, and then foaming the mixture with heat (Japanese Patent Application Laid-Open No.S63-251437 (1988));
c. A method for obtaining a porous water-absorbable resin by dispersing a foaming agent consisting of an azo compound containing an amino group into an aqueous solution containing an unsaturated monomer and crosslinking agent, and by conducting polymerization (Domestic Re-publication of PCT Publication No. WO96/17884);
d. A method of granulating fine particles using water, a hot-melt resin binder and the like;
e. A method of coating the surface of a water-absorbable resin in a composition with porous inorganic particles so that the weight ratio of the resin to the inorganic particles falls within a range of 10/90 to 90/10, wherein the composition consists of a mixture of particles of the water-absorbable resin and the inorganic particles (Japanese Patent Application Laid-Open No.H8-10616 (1996)).

However, these methods were not sufficient in terms of performance and a production process.

Further, it has recently been suggested to improve the absorption speed by a method in which the surface area of a water-absorbable resin is increased by least 10% by building a micro-filler into the water-absorbable resin (International Publication No. WO99/03577).

In said method, the improvement of the absorption speed is recognized for a liquid to be absorbed containing water-insoluble or hardly water-soluble matters such as menstrual blood or feces, however, the further improvement of the absorption speed and absorption amount of the liquid is desired because of the increased demand from the market.

The inventors have intensively studied considering the above-mentioned problems, and as a result, have reached to the present invention with a finding that the diffusion/absorption speed and absorption amount of a liquid to be absorbed are improved by using a water-absorbable resin obtained by polymerization in the presence of a complex compound (d) of a metal element (d1) and a ligand (d2) in which the ligand is an anion or a neutral molecule, in combination with a water-insoluble nonporous spherical monoparticle having a specific average particle diameter.

The present invention is directed to provide absorbents having an excellent diffusion/absorption speed and absorption amount of a liquid to be absorbed inside the absorbable resin, and to provide a process for producing the same, wherein the liquid to be absorbed contains water-insoluble or hardly water-soluble matters such as menstrual blood or feces. Further, the another purpose of the present invention is to provide absorbable constructs and absorbable articles showing an excellent absorption performance when the absorbents of the present invention are applied to sanitary goods such as a sanitary napkin.

SUMMARY OF THE INVENTION

Namely, the present invention is the invention described in (I) through (IV) below.

(I) Absorbents (C) comprising a water-absorbable resin (A) and water-insoluble nonporous spherical monoparticle (B) having an average particle diameter of 1 to 50 nm, and said (A) is a water-absorbable resin obtained by polymerization in the presence of a complex compound (d) of a metal element (d1) and a ligand (d2) in which the ligand is an anion or a neutral molecule.

(II) A process for producing absorbents (C) by mixing said (B) in water-solublizing state with the dry powdery particle of said (A).

(III) Absorbable constructs (F) composed of a matrix of said absorbents (C) and a fibrous material (E), wherein the amount of said absorbents (C) is 30 to 95% by weight based on said absorbable constructs (F).

(IV) Absorbable articles (G) provided with said absorbable constructs (F), a liquid-permeable sheet and an air-permeable back sheet.

DETAILED DISCLOSURE OF THE INVENTION (Absorbents and a Process for Producing the Same)

As the water-absorbable resins (A) mentioned herein, for example, crosslinked starch-acrylic acid salt copolymers, saponified starch-acrylonitrile copolymers, crosslinked polyacrylic acid salts, self-crosslinked polyacrylic acid salts, saponified crosslinked (meth)acrylic ester-vinyl acetate copolymers, crosslinked isobutylene/maleic anhydride copolymers, crosslinked polysulfonic acid salts, crosslinked polyacrylic acid salt/polysulfonic acid salt copolymers, crosslinked polyacrylic acid/polyacrylamide copolymers, crosslinked polyacrylamide and hydrolysis products thereof, crosslinked polyvinylpyrrolidone, crosslinked derivatives of cellulose and the like are can be mentioned.

Among these, preferable water-absorbable resin is a resin which can absorb and hold a large quantity of liquid by ion osmotic pressure and has a polymerizable monomer containing a carboxylic acid salt and/or a carboxylic acid as a main constituent, which monomer gives less leakage of liquid even though a load or an external force is added, and crosslinked starch-acrylic acid salt copolymers and crosslinked polyacrylic acid salts are further preferable.

The kind of the salt and its degree of neutralization are not particularly limited when (A) is a resin in the form of a salt (neutralized salt). The kind of the salt is typically, for example, an alkali metal salt, preferably a sodium or potassium salt and the degree of neutralization for its acid group is typically 50 to 90 mol %, preferably 60 to 80 mol %. The timing of neutralization may be before or after polymerization.

The water-absorbable resin (A) of the above-mentioned crosslinked polyacrylic acid salts is a water-absorbable resin obtained by polymerizing a water-soluble monomer (a-1) and a first crosslinking agent (a-2).

As the water-soluble monomer (a-1) used for producing (A), what can be exemplarily mentioned is a radically polymerizable water-soluble monomer having a carboxylic group, sulfonic acid group and phosphoric acid group, and a salt thereof.

As the radically polymerizable water-soluble monomer having a carboxylic group, what can be exemplarily mentioned is an unsaturated mono- or polycarboxylic acid [(meth)acrylic acid (which means acrylic acid and/or methacrylic acid. Hereinafter, the same description is used), crotonic acid, sorbic acid, maleic acid, itaconic acid, cinnamic acid], its salt or the like, or an anhydride thereof [maleic anhydride or the like], etc.

As the radically polymerizable water-soluble monomer having a sulfonic acid group, for example, what can be mentioned is a fatty acid or an aromatic vinyl sulfonic acid (vinyl sulfonic acid, allyl sulfonic acid, vinyltoluene sulfonic acid, styrene sulfonic acid and the like), sulfoalkyl (meth)acrylate [sulfoethyl (meth)acrylate, sulfopropyl (meth)acrylate or the like], (meth)acrylamido alkylsulfonic acid [2-acrylamido-2-methylpropanesulfonic acid or the like], or a salt thereof, etc.

As the radically polymerizable water-soluble monomer having a phosphoric acid group, for example, such as a (meth)acrylic acid hydroxyalkyl phosphoric acid monoester, [2-hydroxyethyl(meth)acryloyl phosphate, phenyl-2-acryloyloxyethyl phosphate and the like] can be mentioned.

These may be used alone, or 2 or more of them may be used in combination. Among these, the preferable water-soluble monomer is a radically polymerizable water-soluble monomer having a carboxylic group and the salt thereof, more preferably an unsaturated mono- or polycarboxylic acid and the salt thereof, and particularly preferable is (meth)acrylic acid or a salt thereof.

As the crosslinking agent used for producing (A), there are a first crosslinking agent (a-2) used in combination at polymerization of the above monomer, and a surface-crosslinking agent (a second crosslinking agent; a-3) which crosslinks the surface of particle which is prepared as needed by dry-pulverizing after polymerization. As (a-2), for example, what can be mentioned is a crosslinking agent having 2 or more ethylenically unsaturated groups, crosslinking agent having at least one functional group which can react with the functional group of the monomer and having at least one ethylenically unsaturated group, crosslinking agent having at least 2 or more functional groups which can react with the functional group of the monomer, or the like.

(i) As the crosslinking agent having 2 or more ethylenically unsaturated groups, such as N,N'-methylenebis(meth) acrylamide, ethylene glycol di(meth)acrylate, polyethylene glycol di(meth)acrylate, propylene glycol di(meth) acrylate, glycerin (di or tri)acrylate, trimethylolpropane triacrylate, triallylamine, triallylcyanurate, triallylisocyanurate, tetraallyloxyethane, pentaerythritol triallyl ether can be mentioned.

(ii) As the crosslinking agent having at least one functional group which can react with the functional group (for example, a carboxyl group) of the monomer and having at least one ethylenically unsaturated group, a crosslinking agent having at least one functional group which can react with a group such as a carboxylic acid (salt), hydroxyl, amino group and at the same time having at least one ethylenically unsaturated group, and so on can be mentioned, and for example, an ethylenically unsaturated group having an epoxy group such as glycidyl (meth) acrylate etc. and an ethylenically unsaturated group having a hydroxy group such as N-methylol(meth)acrylamide or hydroxyethyl (meth)acrylate, and the like can be mentioned.

(iii) The crosslinking agent having at least 2 or more functional groups which can react with the functional group of the monomer is a crosslinking agent having at least 2 or more functional groups which can react with a group such as a carboxylic acid (salt), hydroxyl, amino group, and as examples of such crosslinking agent, such as a polyglycidyl ether compound having 2 to 10 epoxy groups in a molecule [ethylene glycol diglycidyl ether, glycerin-1,3-diglycidyl ether, glycerin triglycidyl ether, polyethylene glycol diglycidyl ether (the polymerization degree of polyethylene glycol is 2 to 100), polyglycerol polyglycidyl ether (the polymerization degree of polyglycerol is 2 to 100) and the like]; a polyol compound of from divalent to 20-valent [glycerin, ethylene glycol, polyethylene glycol (the polymerization degree is 2 to 100) and the like]; a polyamine compound of from divalent to 20 valent [ethylenediamine, diethylenetriamine and the like]; a polyamine-based resin having a molecular weight of 200 to 500,000 (polyamide polyamine epichlorohydrin resin, polyamine epichlorohydrin resin, and the like), an alkylene carbonate [ethylene carbonate and the like], an azilidine compound, a polyimine compound can be mentioned. These crosslinking agents may be used alone, or 2 or more of them may be used in combination.

The amount of the first crosslinking agent (a-2) used is preferably 0.001 to 5.0% by mass based on the total mass of the monomer (a-1) and the first crosslinking agent (a-2), more preferably 0.002 to 2.0% by mass, and the amount 0.003 to 1.6% by mass is particularly preferred. When the amount of (a-2) is 0.001% by mass or more, the abilities of water retention/blood retention/absorption become good, and when 5.0% by mass or less, the crosslinking is not too strong and also the abilities of water retention/blood retention/absorption do not decrease.

The production process of the water-absorbable resin (A) in the present invention may be process which has been conventionally known, such as a solution polymerization process using an initiator, emulsion polymerization process, suspension polymerization process, reverse-phase suspension polymerization process, thin film polymerization process, spray polymerization process can be mentioned. As a method for controlling polymerization, an adiabatic polymerization method, temperature-control polymerization method, isothermal polymerization method and the like can be mentioned. When a suspension polymerization process or reverse-phase suspension polymerization process is applied to the production process, the polymerization is carried out in the presence of a conventionally known dispersing agent, protective colloid, surfactant or a mixture of one or 2 or more of them if necessary. Further, in case of a reverse-phase suspension polymerization process, the polymerization is carried out using a conventionally known solvent such as cyclohexane, n-hexane, n-heptane and xylene. The solution polymerization process employing a polymerization initiator is preferable, and an aqueous solution polymerization process is particularly preferred because it does not require an organic solvent and the like, and thus it is advantageous from the viewpoint of the production cost.

As an initiator, a conventionally known initiator can be used without particular limitation as long as the initiator is an azo type initiator, peroxide type initiator, redox type initiator or organic halogenated compound initiator. Specifically, those initiators described below can be mentioned.

(i) As the azo type initiator, azobisisobutylonitrile, azobiscyanovaleric acid and its salt, 2,2'-azobis(amidinopropane) dihydrochloride, 2,2'-azobis(2-amidinopropane) hydrochloride, 2,2'-azobis[2-methyl-N-(2-hydroxyethyl)] propionamide and the like;

(ii) as the peroxide type initiator, an inorganic peroxide [hydrogen peroxide, ammonium persulfate, potassium persulfate, sodium persulfate and the like], an organic peroxide [benzoyl peroxide, di-t-butyl peroxide, cumene hydroperoxide, succinic acid peroxide, di(2-ethoxyethyl) peroxydicarbonate and the like];

(iii) as the redox type initiator, a combination of a reducing agent such as a sulfite or bisulfite of an alkali metal, ammonium sulfite, ammonium bisulfite, ferric chloride, ferric sulfate, ascorbic acid, and with an oxidizing agent such as a persulfate of an alkali metal, ammonium persulfate, hydrogen peroxide, organic peroxide can be mentioned.

(iv) The halogens of the organic halogenated compound initiators are fluorine, chlorine, bromine and iodine.

Though there is no particular limitation for the organic halogenated compound, what is preferred from the viewpoint of the polymerizability is an organic halogenated compound having a halogen atom number of 1 to 10 or more and having a carbon atom number of 1 to 15 or more, selected from a group consisting of a halogenated alkyl, halogenated alkyl phenyl ketone, halogenated alkylcarboxylic acid and alkyl ester of halogenated alkylcarboxylic acid. Tetrachloromethane, trichlorobromomethane, trichloroiodomethane, dichloromethyl phenyl ketone, 1-bromo-1-methylethylcarboxylic acid and an alkyl ester of 1-bromo-1-methylethylcarboxylic acid wherein the alkyl group has a carbon atom number of 1 to 8 (for example, methyl 1-bromo-1-methylethyl carboxylate, ethyl 1-bromo-1-methylethyl carboxylate, octyl 1-bromo-1-methylethyl carboxylate, and lauryl 1-bromo-1-methylethyl carboxylate) are more preferred. Dichloromethyl phenyl ketone and an alkyl ester of 1-bromo-1-methylethyl carboxylic acid in which the carbon number in the alkyl group is 1 to 8 are particularly preferred.

These initiators may be used alone, or 2 or more of them may be used in combination. The azo type initiator, the redox type initiator and a combination of both are preferable. The amount of the initiator used is preferably 0.005 to 0.5% by mass based on the total mass of (a-1) and (a-2), more preferably 0.007 to 0.4% by mass and particularly preferably 0.009 to 0.3% by mass.

Further, it is preferable to make said (A) have a high molecular weight in order to enhance the absorption performance of the water-absorbable resin (A) of the present invention, and for the above purpose said (A) can be obtained by any one of the methods of 1) through 3) described below.

1) Polymerization is carried out under a condition in which the concentration of the total amount of (a-1) and (a-2) in a polymerization liquid is 20% by mass or less.
2) Polymerizing 70% by mass or more of the polymerizable monomers ((a-1) and (a-2)) in the polymerization liquid at a constant polymerization temperature of 60° C. or less, wherein the controlled range for the constant temperature is preferably ±5° C., and more preferably ±2° C.
3) Polymerization is carried out in the presence of a complex compound (d) of a metal element (d1) and a ligand (d2), in which the ligand is an anion or a neutral molecule.

As the water-absorbable resin (A) of the present invention, the one obtained by 3) is particularly preferred.

The complex compound (d) is a complex compound of a metal element (d1) and a ligand (d2) of an anion or a neutral molecule, and has a structure in which (d1) is surrounded by the ligand (d2) of an anion or a neutral molecule.

As for (d1), there is no particular limitation so far as it is a metal element, and for example, the IA Group element metal (lithium, sodium, potassium, cesium and the like), IB Group element metal (copper, silver, gold and the like), IIA Group element metal (magnesium, calcium, barium and the like), IIIA Group element metal (scandium, yttrium and the like), IIIB Group element metal (aluminum, gallium, indium, thallium and the like), IVA Group element metal (titanium, zirconium, hafnium and the like), IVB Group element metal (tin, zinc and the like), VA Group element metal (vanadium, niobium, tantalum), VB Group element metal (antimony, bismuth and the like), VIA Group element metal (chromium, molybdenum, tungsten), VIB Group element metal (tellurium, polonium and the like), VIIA Group element metal (manganese, technetium, rhenium), VIII Group element metal (iron, cobalt, nickel, ruthenium, rhodium, palladium, osmium, iridium, platinum), Lanthanoid Group element metal (lanthanum, cerium and the like), the Actinoid Group element metal (actinium, thorium and the like) and the like, all of which are the principal group element metals, can be mentioned. From the viewpoint of the polymerizability of a vinylic polymerizable monomer, the IB Group, IIIA Group, IVA Group, VA Group, VIA Group, VIIA Group, VIII Group and Lanthanoid Group element metals are preferable, the IB Group, VIII Group and Lanthanoid Group element metals are more preferable, and the IB Group and VIII Group element metals of the $4^{th}$ to $6^{th}$ period are particularly preferable. From the viewpoint of easy-to-handle workability and so on, the VIII Group element metals of the $5^{th}$ period (ruthenium, rhodium, palladium) are most preferable.

Though said (d1) exists usually as a cation, it can be otherwise than a cation, for example, it may be neutral as iron pentacarbonyl.

(d2) is not specifically limited so far as it is a ligand being an anion or neutral molecule, but for example, 1) the anion of an atom selected from hydrogen and halogen, 2) a compound having one or two or more atoms selected from nitrogen, oxygen, phosphorous and sulfur, and 3) one or two or more compounds selected from conjugated system compounds.

Specifically, those described below can be mentioned.

1) The anion of an atom selected from hydrogen and halogen;
   the anion of hydrogen, fluorine, chlorine, bromine and iodine;

2) As the compound having one or two or more atoms selected from a group consisting of nitrogen, oxygen, phosphorous and sulfur, those described below can be mentioned. A compound having a molecular weight of 1,000 or less is preferable (those having the possibility that the kind of coordination is 2 or more were classified in either group suspected to coordinate).

(1) Tertiary phosphine compounds having 1 to 4 or more phosphorous atoms and 3 to 42 or more carbon atoms;

trimethylphosphine, triethylphosphine, diethylphenylphosphine, triphenylphosphine (hereinafter, referred to as $PPh_3$), ortho-phenylenebis(diphenylphosphine), ortho-phenylenebis(dimethylphosphine), ortho-phenylenebis(diethylphosphine), ortho-phenylenebis(ethylphenylphosphine), 1,2-bis(diphenylphosphino)ethane, 1,2-bis(dimethylphosphino)ethane (hereinafter, referred to as dppe), 1,2-bis(diethylphosphino)ethane, 1,2-bis(ethylphenylphosphino)ethane, 1,2-bis(diphenylphosphino)methane (hereinafter, referred to as dppm), 1,2-bis(dimethylphosphino)methane, 1,2-bis(diethylphosphino)methane, 1,2-bis(ethylphenylphosphino)methane, tris(diphenylphosphinoethyl)phosphine, tris(diethylphosphinoethyl)phosphine, tris(dimethylphosphinoethyl)phosphine, tris(ethylphenylphosphinoethyl)phosphine, and the like;

(2) Ammonia or amines having 1 to 4 or more nitrogen atoms and 0 to 44 or more carbon atoms;

(2-1) the number of nitrogen atom is 1; pyridine (hereinafter, described as py), diethylamine, salicylamine, aminoethaneselenole, 2-hydroxy-6-methylpyridine, 2-(diethylamino)ethanol, bis(2-aminoethyl)amide, ethanolamine, 2-aminoethanol, β-alanine, 2-hydroxy-6-methylpyridine, 3-salicylideneamino-1-propanol, 2-pyrrolidone, 8-quinolinol, salicylaldimine, α-picoline and the like;

(2-2) the number of nitrogen atom is 2; ethylenediamine (hereinafter, referred to as en), propylenediamine, trimethylenediamine, 1,2-cyclohexanediamine, N,N-diethylethylenediamine, N,N-dimethylethylenediamine, salicylideneethylenediamine, N-ethylsalicylaldiamine, bis(benzoylacetone)ethylenediamine, 1,2-diamino-1,1'-dimethylethane, 2,2'-bipyridine (hereinafter, referred to as bpy), 2,2'-bipyridin-3-ine, 2,2'-bipyridine-N,N'dioxide, dicyandiamidine, (aminoiminomethyl)urea, [(2-aminoethyl)amino]-1-propanol, 2-[(3-aminopropyl)amino]ethanol, N-2[2(diethylamino)ethyl]-3-amino-1-propanol, tris [2-(methylamino)ethyl]amine, imidazole, N,N'-disalicylidenetrimethylenediamine, 4,6,6-trimethyl-3,7-diazanona-3-en-1,9-diol, N,N,N',N'-tetramethylethylenediamine, 1,8-naphtylidine, and the like;

(2-3) the number of nitrogen atom is 3 or more; diethylenetriamine, triethylenetetramine, tetraethylpentamine, N,N'-bis(2-aminobenzylidene)ethylenediamine, tris[2-(methylamino)ethyl]amineaminopyridine, 1,3-bis[bis(2-pyridylethyl)aminomethyl]benzene, 4-dimethylamino-2,3-dimethyl-1-phenyl-5-pyrazolane, biguanide, imidodicarbonimidediamide, biuret, carbamoylguanidine, phthalocyanine, N,N,N',N'-tetrakis(2-aminoethyl)ethylenediamine, 1,2,3-triaminopropane, tris(2-benzimidazolylmethyl)amine, tetrakis(2-pyridylmethyl)ethylenediamine, 2,2',2''-terpyridine, 1,4,7,10-tetraazadecane, 1,4,8,11-tetraazaundecane, 1,5,8,12-tetraazadodecane, 1,4,8,11-tetraazacyclotetradecane, ethylenebis(biguanide), tetraphenylporphyrin, tris(2-pyridylmethyl)amine, histidine and the like;

(3) the carbonyl-containing compounds having 1 to 3 or more carbonyl groups and 3 to 40 or more carbon atoms (excluding carboxylic acid);

ethyl acetoacetate, acetylacetone (hereinafter, referred to as acac), 2,4-pentanedione, bis(acetylacetone), 3-methylpentane-2,4-dione, 1-phenyl-1,3-butanedione, 3-phenylpentane-2,4-dione, 1,3-diphenyl-1,3-propanedione, 1-phenyl-1, 3,5-hexanetrione, 5,5'-(1,2-ethanediyldinitrilo)bis(1-phenyl-1,3-hexanedione), trifluoroacetylacetone, hexafluoroacetylacetone, benzyl, dibenzoylmethane, aspartic acid benzoylacetone, thenoyltrifluoroacetone, 4,4'-(1,2-ethanediyldinitrilo)bis(2-pentanone), dipivaloylmethane and the like;

(4) carboxylic acids containing 1 to 4 or more carboxylic acid groups and 2 to 20 or more carbon atoms;

oxalic acid, malonic acid, salicylic acid, phthalic acid, nicotinic acid, picolinic acid, aspartic acid, benzoylpyruvic acid, ethylenediaminediacetic acid, nitrilotriacetic acid, N'-(2-hydroxyethyl)ethylenediaminetriacetic acid, propylenediaminetetraacetic acid, ethylenediaminetetraacetic acid, trans-1,2-cyclohexanediaminetetraacetic acid, trans-1,2-(cyclohexanedinitrilo)tetraacetic acid, 1,2-(ethanediyldinitrilo) tetraacetic acid, ethylenediaminetetrapropionic acid, glycine, N-methylglycine, glycylglycine, glycylglycylglycylglycine, salicylideneglycine, iminodiacid, methyliminodiacid, N,N-diethyldiselenocarbamic acid, methionine, proline, sarcosine, xanthic acid and the like;

(5) oximes having 1 to 4 or more oxime groups and 2 to 20 or more carbon atoms;

dimethylglyoxime, 3-(2-aminoethylimino)-2-butanoneoxime, benzylmethylglyoxime, 2,6-diacetylpyridinedioxime, 2-pyridylaldoxime, 3-phenylimino-2-butanoneoxime, salicylaldehydeoxime and the like;

(6) phenols having 1 to 4 or more phenol groups and 6 to 30 or more carbon atoms;

catecol, 1,2-benzenediol, 1,3-bis[bis(2-pyridylethyl)aminomethyl]phenol, 2,6-bis[bis(2-pyridylethyl)aminomethyl]-4-phenol, 1-nitroso-2-naphthol and the like;

(7) ethers having 1 to 8 or more ether groups and 4 to 30 or more carbon atoms;

tetrahydrofuran, 1,4-dioxane, 1,4,7,10-tetraoxacyclotetradecane, 1,4,7,10,13-pentaoxacyclopentadecane, 1,4,7,10,13,16-hexaoxycyclooctadecane, 4,7,13,16-tetraoxa-1,10-diazacyclooctadecane, 4,7,13,18-tetraoxa-1,10-diazabicyclo [8,5,5]icosane, 2,3-benzo-1,4,7,10,13-pentaoxacyclopentade-2-cen, 4,7,13,16,21-pentaoxa-1,10-diazabicyclo[8,5,5]tricosane, monensin, nigericin and the like;

(8) sulfur compounds having 1 to 4 or more sulfur atoms and 2 to 40 or more carbon atoms;

diethyldithiocarbamic acid, ethylthioglycolic acid, ethylenebisthioglycolic acid, ethylenethiourea, phenyldithioacetic acid, dithiobenzoic acid, 1,2-aminoethanethiol, diphenylthiocarbazone, dimethylsulfoxide, 2,4-pentanedithione, 2,2,7,7-tetramethyl-3,6-dithiaoctane, 2-imidazolidinethione, dimethyldithiocarbamic acid, thiourea, cysteine, maleonitriledithiol, 1,4,8,11-tetrathiaundecane and the like;

(9) amide compounds having 1 to 3 or more amide groups and 3 to 54 or more carbon atoms;

diazoamide, N,N-dimethylacetamide, N,N-dimethylformamide, hexamethylphosphoric triamide, diphenylphosphinic amide, aminoethylamide, oxamide, valinomycin, phthalimide, succinimide, valinomycin and the like;

(10) N-oxides having 1 to 3 or more N-oxide groups and 6 to 20 or more carbon atoms;

α-picoline-N-oxide, γ-picoline-N-oxide, pyridine-N-oxide and the like;

(11) others;
nitrogen molecule, water, carbon monoxide, urea, salicylaldehyde, N-nitrosophenylhydroxylamine oxyhydrogen and the like.

3) As the conjugated system compound having 2 to 10 or more unsaturated groups and 4 to 14 or more carbon atoms, those described below can be mentioned;
1,5-cyclooctadiene (hereinafter, referred to as cod), 1,3,5,7-cyclooctatetraene, cyclopentadienyl, pentamethylcyclopentadienyl, tropolone, 1,10-phenanthroline and the like.

From the viewpoint of polymerizability for the vinyl group, a halogen (fluorine, chlorine, bromine and iodine) ion and a phosphorous atom-containing compound are preferable, and the anion of an atom selected from chlorine, bromine and iodine and a tertiary phosphine compound are particularly preferred. Further, as a combination, preferably, the combination between the metal element (d1) selected from the VIII Group element of the $5^{th}$ period and the ligand (d2) of an anion or neutral molecule being a halogen ion and/or tertiary phosphine compound can be mentioned.

With regard to the synthesis method of the complex compound (d), it is usually obtained by mixing a salt of (d1) (for example, a halide of a metal, and the like) and (d2) at room temperature. Further, there is also a case in which a compound of interest is prepared after forming a different intermediate complex compound. The salt of (d1) and the ligand of (d2) may be mixed as they are or after each of them being dissolved in a separate aqueous/solvent solution, or may be mixed in an aqueous/solvent solution. If necessary, they may be heated to from 30 through 200° C. When a substance, which should be removed, is generated, it may be removed under reduced pressure. The compound (d) generated may be taken out as it is or as a crystal, and then purified. As the solvent used herein, for example, an alcohol-based solvent (methanol, ethanol and the like), ketone-based solvent (acetone, methyl ethyl ketone and the like), amide-based solvent (N,N-dimethylformamide, N-methylpyrrolidone and the like), sulfoxide-based solvent (dimethyl sulfoxide and the like), and a mixture of 2 or more of them may be mentioned.

There are so many compounds for (d), and they can be synthesized individually by methods described in, for example, Angew. Chem. Int. Ed. Engl., Vol. 12, pp. 57 (1973); J. Chem. Educ., Vol. 50, pp. 343 (1973); Accts. Chem. Research, Vol. 3, pp. 105 (1970); Chem. Rev., Vol. 73, pp. 487 (1973); Interscience-Wilry (1968); Chem. Soc. Rev., Vol. 4, pp. 27 (1975); Basic Inorganic Chemistry (written by F. A. Cotton and G. Wilkinson, Baifukan Co., Ltd.); Inorganic Compound-Complex Dictionary (K. Nakahara, Kodansha Ltd.), etc.

The mode of coordination is not specifically limited, and there are monodentate (for example, triphenylphosphine as a ligand), bidentate (for example, ethylenediamine as a ligand), multidentate mode having 3 to 6 coordination sites (for example, terpiridine as a ligand), but a combination of these coordination modes is usually applied. Further, (d) is usually a non electrolyte type complex compound having no charge, but may be an electrolyte type complex compound having charge such as a complex cation and a complex anion.

As (d), those described below may be specifically mentioned.

As specific examples,
(1) when (d1) is the IB Group element metal, $[Cu(CH_3)(PPh_3)]$, $[Cu_2Cl(cod)_2]$, $[Ag(py)_2Cl]$, $[Ag(py)_4Cl]$, $[Ag(py)_4]Cl_2$, $[AuCl(PPh_3)]$, $[AuCl_3(PPh_3)]$, and $[Au(dppe)]Cl$, or the like;

(2) when (d1) is the VIII Group element metal of the $4^{th}$ period, $[FeCl_2(bpy)_2]$, $[FeCl_2(bpy)_2]Cl$, $[FeCl(H)(CO)(PPh_3)_3]$, $[FeCl(H)(dppe)_2]$, $[FeCl_3(NO)(PPh_3)_2]$, $[FeCl_2(PPh_3)_3]$, $[FeCl_2(PPh_3)_4]$, $[Fe(CN)_2(bpy)_2]$, $[Fe(CO)_2(PPh_3)_3]$, $[Fe(H)_2(N_2)(PPh_3)_3]$, $[CO_2Cl_2(cod)_2]$, $[CoCl(CO)(PPh_3)_2]$, $[CoCl(PPh_3)_3]$, $[CoCl(O_2)(PPh_3)_3]$, $[CoCl_3(py)_3]$, $[Co(cod)_2]Cl$, $[Co(H)(CO)(PPh_3)_3]$, $[Ni(acac)Cl(PPh_3)]$, $[NiBr(CH_3)\{P(C_2H_5)_3\}_2]$, $[NiBr(NH_3)_3]$, $[Ni(CH_3)Cl(cod)]$, $[Ni(C_2H_5)(cod)]Cl$, $[Ni(CH_3)(PPh_3)]$, $[Ni_2Cl_2(acac)_2]$, $[NiCl_2(bpy)]$, $[NiCl_2(cod)]$, $[Ni_2Cl_2(dppm)]$, $[NiCl_2(en)]$, $[NiCl_2(NH_3)(PPh_3)]$, $[NiCl_2(PPh_3)]$, $[Ni_2Cl_4(PPh_3)_2]$, $[Ni(PPh_3)_4]$, $[Ni(py)_4]Cl_2$, $[Ni(SO_3)(H_2O)_3]$, and $[Ni(SO_3)(NH_3)_3]$, or the like;

(3) when (d1) is the VIII Group element metal of the $5^{th}$ period, $[Rh_2Cl_2(cod)_2]$, $[RhCl(CO)(PPh_3)_2]$, $[RhCl(PPh_3)_3]$, $[RhCl(O_2)(PPh_3)_3]$, $[RhCl_3(py)_3]$, $[Rh(cod)_2]Cl$, $[Rh(H)(CO)(PPh_3)_3]$, $[RuCl_2(bpy)_2]$, $[RuCl_2(bpy)_2]Cl$, $[RuCl(H)(CO)(PPh_3)_3]$, $[RuCl(H)(dppe)_2]$, $[RuCl_3(NO)(PPh_3)_2]$, $[RuCl_2(PPh_3)_3]$, $[RuCl_2(PPh_3)_4]$, $[Ru(CN)_2(bpy)_2]$, $[Ru(CO)_2(PPh_3)_3]$, $[Ru(H)_2(N_2)(PPh_3)_3]$, $[Pd(acac)Cl(PPh_3)]$, $[PdBr(CH_3)\{P(C_2H_5)_3\}_2]$, $[PdBr(NH_3)_3]$, $[Pd(CH_3)Cl(cod)]$, $[Pd(C_2H_5)(cod)]Cl$, $[Pd(CH_3)(PPh_3)]$, $[Pd_2Cl_2(acac)_2]$, $[PdCl_2(bpy)]$, $[PdCl_2(cod)]$, $[Pd_2Cl_2(dppm)]$, $[PdCl_2(en)]$, $[PdCl_2(NH_3)(PPh_3)]$, $[PdCl_2(PPh_3)]$, $[Pd_2Cl_4(PPh_3)_2]$, $[Pd(PPh_3)_4]$, $[Pd(py)_4]Cl_2$, $[Pd(SO_3)(H_2O)_3]$, and $[Pd(SO_3)(NH_3)_3]$, or the like;

(4) when (d1) is the VIII Group element metal of the $6^{th}$ period, $[OsCl_2(bpy)_2]$, $[OsCl_2(bpy)_2]Cl$, $[OsCl(H)(CO)(PPh_3)_3]$, $[OsCl(H)(dppe)_2]$, $[OsCl_3(NO)(PPh_3)_2]$, $[OsCl_2(PPh_3)_3]$, $[OsCl_2(PPh_3)_4]$, $[Os(CN)_2(bpy)_2]$, $[Os(CO)_2(PPh_3)_3]$, $[Os(H)_2(N_2)(PPh_3)_3]$, $[Ir_2Cl_2(cod)_2]$, $[IrCl(CO)(PPh_3)_2]$, $[IrCl(PPh_3)_3]$, $[IrCl(O_2)(PPh_3)_3]$, $[IrCl_3(py)_3]$, $[Ir(cod)_2]Cl$, $[Ir(H)(CO)(PPh_3)_3]$, $[Pt(acac)Cl(PPh_3)]$, $[PtBr(CH_3)\{P(C_2H_5)_3\}_2]$, $[PtBr(NH_3)_3]$, $[Pt(CH_3)Cl(cod)]$, $[Pt(C_2H_5)(cod)]Cl$, $[Pt(CH_3)(PPh_3)]$, $[Pt_2Cl_2(acac)_2]$, $[PtCl_2(bpy)]$, $[PtCl_2(cod)]$, $[Pt_2Cl_2(dppm)]$, $[PtCl_2(en)]$, $[PtCl_2(NH_3)(PPh_3)]$, $[PtCl_2(PPh_3)]$, $[Pt_2Cl_4(PPh_3)_2]$, $[Pt(PPh_3)_4]$, $[Pt(py)_4]Cl_2$, $[Pt(SO_3)(H_2O)_3]$, and $[Pt(SO_3)(NH_3)_3]$, or the like can be mentioned, though, they are not for the limiting purpose and therefor the compounds within the scope previously described may be employed.

A preferred complex compound is such as $[RuCl_2(PPh_3)_3]$, $[RuCl_2(PPh_3)_4]$, $[Pd_2Cl_2(dppm)]$, $[RhCl(CO)(PPh_3)_2]$ and $[RhCl(PPh_3)_3]$, i.e., the one containing the VIII Group element metal (ruthenium, rhodium, palladium) of the $5^{th}$ period and a ligand selected from a group consisting of an anion of an atom, which atom is selected from chlorine, bromine and iodine, and a tertiary phosphine compound.

Further, from the viewpoints of polymerizability and operability, it is preferable that (d) is a complex compound which is soluble in water or a water-soluble organic solvent. As the water-soluble organic solvent, the same solvent as used for the synthesis of the (d) may be mentioned.

The amount of (d) and (d1) is preferably 0.005 ppm to 2.0% by mass for (d) and 0.001 ppm to 1.0% by mass for (d1) based on the total mass of a monomer and first crosslinking agent, and more preferably 0.0.1 ppm to 1.0% by mass for (d) and 0.005 ppm to 0.5% by mass for (d1), and most preferably, 0.02 ppm to 0.6% by mass for (d) and 0.01 ppm to 0.3% by mass for (d1).

When the amount of (d) is 0.005 ppm to 2% by mass and the amount of (d1) is 0.001 ppm to 1% by mass, the ability as an absorbable article is performed, and productivity is good as well because the polymerization speed and the polymerization yield are to be sufficient.

When the solubility of (d) to an aqueous polymerization liquid is low, the polymerization can also be carried out by using a water-soluble organic solvent and surfactant in combination and by dissolving or dispersing them in the aqueous polymerization liquid of the monomer.

The water-absorbable resin (A) obtained by the method can be further crosslinked if necessary by kneading the resin in a state of a water-containing gel with the crosslinking agent (a-2) or polyvalent metal compound capable of forming an ionic crosslinkage (such as calcium chloride, magnesium sulfate, aluminum sulfate) or the like. Relatively homogeneous crosslinking is thereby obtained, thus the water-absorbable resin having high gel strength and fewer amounts of water-soluble components can be produced.

The effect of the present invention can be further improved when the absorbable resin (A) is crosslinked with a crosslinker (the second crosslinking agent) at its surface, wherein the surface-crosslinked resin is formed by crosslinking the vicinity of the surface of a crosslinked polymer obtained by drying and by subsequently pulverizing the water-containing gel-stated polymer of the absorbable resin produced from the above method, and, if necessary, by adjusting the grain size of the pulverized polymer.

The drying method may be usual methods such as a drying method by hot air at a temperature of 80 to 230° C., thin film drying method using a drum dryer heated at 100 to 230° C., (heated) reduced pressure drying method, freeze drying method and drying method by infrared rays. Also, there is no limitation for the pulverizing method, and common equipment such as a hammer type pulverizer, impact type pulverizer, roll type pulverizer and jet stream type pulverizer may be used. The obtained pulverized material, if necessary, are sieved to adjust its grain size. The form of the crosslinked polymer after pulverization is not specifically limited, and irregular pulverized form, flake form, pearl form, rice grain form, granulated form and the like can be exemplified. For the usage in paper diapers and the like, the irregular pulverized form is preferable from the viewpoints that it entangles well with a fibrous material and that its falling from the fibrous material may not be anticipated.

The grain size of the obtained water-absorbable resin (A) in the particle form is controlled by sieving when needed. The mass average particle diameter of (A) obtained is preferably 100 to 800 µm, and further preferably 200 to 500 µm and, the one which was pulverized to have 95% by mass or more of particles within a range of 100 to 850 µm can be used. It is preferable that the content of a fine particle is less. The content of the particle of 100 µm or less is preferably 3% or less, and more preferably, the content of the particle of 150 µm or less is 3% or less. The mass average particle diameter is measured according to a method by plotting the respective grain size distribution of the water-absorbable resin on a logarithmic probability paper in which a horizontal axis represents the particle diameter and a longitudinal axis represents the content based on mass, and determining a particle diameter which contains the 50% point of the total mass.

As the method of surface-crosslinking the water-absorbable resin (A), the conventional method, for example, a method of mixing a mixed solution containing the second crosslinking agent (a-3), water and an organic solvent with (A) and reacting the mixture with heat can be mentioned.

The agent (a-3) may be the same or different as (a-2) above, however, the crosslinking agent (iii) having at least two functional groups which can react with an acid group such as a carboxylic acid and/or a group of their salts is preferable, and a polyglycidyl ether compounds such as ethylene glycol diglycidyl ether, polyamine resin and azilidine compound are preferable in particular from the viewpoint that they can conduct the surface-crosslinking at a comparatively low temperature.

The amount of (a-3) used is preferably 0.001 to 7.0% by mass based on the total amount of (a-1), (a-2) and (a-3), more preferably 0.002 to 5.0% by mass, and particularly preferably 0.003 to 4.0% by mass. When the amount of (a-3) used is 0.001% by mass or more, the degree of surface-crosslinking is adequate, and the effect of improvement for the absorption amount under a load is also to be sufficient. On the other hand, when the amount of (a-3) used is 7.0% by mass or less, the degree of surface-crosslinking is not excessive, and the amount of the water/blood retention is not lowered.

The amount of water used when the surface-crosslinking is conducted is preferably 1 to 10% based on the mass of the water-absorbable resin (A) and more preferably 2 to 7%. When the amount of water used is 1% or more, the permeation of (a-3) to the inside of particles of the water-absorbable resin (A) is to be sufficient, and the improvement effect of the absorption amount under a load, particularly, the absorption amount under a heavy load (for example, 60 g/cm$^2$) is to be good. On the other hand, when the amount of water used is 10% or less, the permeation of (a-3) to the inside of (A) is not excessive, the improvement of the absorption amount under a load is confirmed, and the problem of a great decrease in the water/blood retention amount does not occur.

In the present invention, as the kind of the organic solvent used in combination with water, a conventionally known hydrophilic solvent can be used, and it can be suitably selected with the consideration of the degree of permeation of (a-3) to the inside of (A) and of the reactivity of (a-3) and the like. The hydrophilic organic solvents capable of being dissolved in water, such as methanol and diethylene glycol, are preferable. These solvents may be used alone, or 2 or more of them may be used in combination.

The amount of the solvent used can be variously changed depending on the kind of the solvent, but is preferably 1 to 10% based on the mass of (A). Further, the ratio of the solvent to water can be also arbitrarily changed, and is preferably 20 to 80% based on mass and more preferably 30 to 70%.

A mixed solution containing (a-3), water and a solvent is added to and mixed with (a2) by a conventionally known method, and a reaction with heat is carried out. The reaction temperature is preferably 80 to 200° C. and more preferably 100 to 160° C. The reaction time can be changed depending on the reaction temperature, but is preferably 3 to 60 minutes and more preferably 5 to 40 minutes.

The particulate water-absorbable resin (A) obtained by surface-crosslinking like this can be further additionally surface-crosslinked by the same kind of (a-3) or the different kind of (a-3).

The thus obtained particulate water-absorbable resin (A) is sieved and the grain size is adjusted if necessary. The mass average particle diameter of (A) obtained is hardly changed compared to that before surface-crosslinking, and preferably 100 to 800 µm and further preferably 200 to 500 µm. The resin which was pulverized to have 95% by mass or more particles within a range of 100 to 850 µm can be used. It is preferable that the content of fine particles is less. The content of particles of 100 μm or less is preferably 3% or less, and more preferably the content of particles of 150 μm or less is 3% or less.

These surface-crosslinked type crosslinked copolymer is preferable because its absorption performance is superior not only under normal pressure but also under a load, and because its gel strength increases.

The average particle diameter of the water-insoluble nonporous spherical monoparticles (B) having an average particle diameter of 1 to 50 nm used in the present invention is preferably 3 to 40 nm, more preferably 5 to 35 nm and most preferably 10 to 30 nm.

When the average particle diameter is less than 1 nm, the diffusion and absorption speed of a liquid to the inside of the resin in the obtained absorbent is bad. Further, when it exceeds 50 nm, the diffusion and absorption speed of a liquid to the inside of the resin in the obtained absorbent is also bad. The average particle diameter can be measured by usual methods such as, for example, calculation from a value obtained from the BET method, the Sears method or a laser method.

The particle (B) is a nonporous spherical monoparticle. With a porous particle, the diffusion and absorption speed becomes bad. Further, its form is spherical. Form other than spherical form such as, for example, hollow form, porous form, petal form, aggregated form or granulated form generates a problem in terms of handling. That said (B) has spherical form can be grasped by observing the particles in a dispersed state by means of, for example, the transmission electron microscope (for example, H-7100FA type, manufactured by Hitachi, Ltd.) under the condition of accelerating voltage of 100 KV. Further, there is a preferable specific surface area for (B) from the viewpoint of the improvement of the diffusion and absorption speed, and that is 50 to 400 $m^2/g$. It is more preferably 75 to 350 $m^2/g$ and particularly preferably 100 to 300 $m^2/g$. The specific surface area can be measured by the BET method, a Blaine method and the like. With regard to the spherical form, the roundness can be grasped, for example, by comparing the specific surface area measured by the BET method with a value of the specific surface area calculated from an average particle diameter measured by a method other than the BET method with the assumption that the particle is monoparticle. The specific surface area (i) calculated from the average particle diameter of the particles of the invention in the present application is close to the measured value of the specific surface area (ii) according to the BET method. It is preferable that the value of (i) is 90 to 110% relative to the value of (ii).

Aggregation of monoparticles is equal to being in the porous state since space is created among the aggregated particles, therefore, the average particle diameter will increase and the specific surface area will decrease. Accordingly, the presence proportion between the monoparticles (primary particles) and the aggregated particles (secondary particles) can be controlled with the average particle diameter and specific surface area. Although the primary particles of Aerosil 200 (silica manufactured by Nippon Aerosil Co., Ltd.) is 60 nm or less, they are aggregated and not dispersed to be primary particles even if they are dispersed or solubulized in water, therefore the average particle diameter is usually 100 nm or more, so it is not used in the present application. It is considered that this may be presumably because the primary particles having been aggregated in the drying step in the production of the particles are hardly returned to their original primary particles even if they are dispersed in water. It is important not to dry the primary particles before use.

The kind of the material of (B) is not specifically limited as long as its average particle diameter is 1 to 50 nm and as long as it is water-insoluble and nonporous, and the material may be either organic or inorganic.

As the example of organic nonporous spherical monoparticles, for example,
(i) organic nonporous spherical monoparticles consisting only of the carbon atom; polyethylene, polypropylene, polystyrene, poly-β-xylylene, polybutadiene and the like,
(ii) organic nonporous spherical monoparticles consisting of the carbon atom and oxygen atom; a polyacrylate, polymethacrylate, polyvinyl acetate, polyvinyl ether, thermoplastic polyester, polycarbonate, polyphenylene oxide, polyepoxy, polyacetal, cellulose derivative and the like,
(iii) organic nonporous spherical monoparticles containing the nitrogen atom; a polyacrylonitrile, polyamide, thermoplastic polyurethane and the like,
(iv) other organic nonporous spherical monoparticles; polyvinyl chloride, polyvinylidene chloride, a fluororesin, polysulfone and the like, and a polymer obtained by copolymerizing 2 or more monomers which constitute these resins can be mentioned. The example (i) is preferable. Further, the particles are required to have a melting temperature equal to or higher than a temperature for drying to prevent the organic nonporous spherical particles from melting when the water-containing gel is dried. With respect to the balance with the drying temperature, the melting temperature of the organic nonporous spherical monoparticles is usually 130° C. or more and preferably 150° C. or more.

The inorganic nonporous spherical monoparticles may be natural inorganic materials or synthetic inorganic materials, and for example, a silicon oxide, aluminum oxide, iron oxide, titanium oxide, magnesium oxide and zirconium oxide can be mentioned. Further, these may be used in combination of 2 or more of them, or 2 or more of them may form a composite.

Among these, inorganic nonporous spherical monoparticles are preferable, a silicon oxide is further preferable, and amorphous silicon oxide is preferable in particular.

When (B) is used as a water dispersion liquid or water-solublizing liquid having the (B) concentration of 10% by mass, the pH is not specifically limited, but is usually 2 to 11, and preferably, 2.5 to 10 from the viewpoint that (B) can exist stably as the primary particles and the secondary aggregate does not generate at the pH.

The amount of the nonporous spherical monoparticles (B) against the water-absorbable resin (A) is preferably 0.01 to 5.0% by mass, further preferably 0.02 to 3.0% by mass, and particularly preferably 0.04 to 2.5% by mass. When the amount of (B) added is 0.01% by mass or more, the effect of improvement in diffusion and absorption speed to the inside of the resin is observed. When it is 5.0% by mass or less, the improvement in diffusion and absorption speed is attained, and at the same time, the mechanical strength of the obtained absorbent particles is strong. Further, the absorption magnification of the obtained absorbents, the amounts of water/blood retention, and the absorption amount when pressed are not lowered.

The particle (B) is mixed with (A). (B) may be compounded at any step in the manufacture process of (A) from the polymerization step to before and after the drying.
(i) When (B) is compounded before drying, it may be added to a polymerization liquid to form a mixture by polymerization, in which mixture (B) is compounded in a polymer (A) in the water-containing gel state, or may be added to the polymerized polymer in the water-containing gel state to form a mixture. The mixing may be carried out by usual mixing equipment described below, and there is no problem with the mixing temperature as long as it is between the polymerization temperature and room temperature. The mixing time is preferably for 30 minutes to 5 hours.

In this case, since the nonporous spherical monoparticles are compounded to the resin in the water-containing gel state, diffusion and absorption speed of a liquid to the inside of the resin is improved by evaporating moisture in the water-containing gel, and therefore by storing (building) the nonporous spherical monoparticles in the inside of a resin.

(ii) When (B) is compounded after drying, the nonporous spherical monoparticles cover the particle surface of (A), or (A) and the nonporous spherical monoparticles exist separately as a simple mixture of both. In this case, there are effects which not only prevent the phenomenon of association among (A) via water, but also prevent the phenomenon of provoking a decrease in performance caused by coating the surface of (A) with the liquid to be absorbed containing a water-insoluble matters and a water-hardly soluble matters. It is considered that this is the same as the principle using a filtration aid in order to prevent plugging when filtering with a filter.

Methods of (i) and (ii) may be used in combination. In these methods the method of (ii) is preferable.

(B) is in a condition of monoparticles, namely the condition of not aggregated, and it is preferable that the water dispersion liquid of (B), emulsified substance of (B) or water-solublizing state substance of (B) is mixed with (A). The method of mixing (B) in the water-solublizing state with (A) is particularly preferred. Because the water-solubilization tends to disperse the secondary particles into the primary particles. The solubilized state indicates a phenomenon that a substance insoluble in a solvent is visually observed to have been dissolved, and can be judged macroscopically. A colloid state is also included in the solubilized state. The solubilized state can be measured by a transmission factor, and the transmission factor is preferably 80% or more and more preferably 90% or more. The transmission factor can be measured by a spectrophotometer. The water dispersion liquid or water-solublizing state substance can be mixed by usual mixing equipment, but it is important that particles are not left in a dry condition from the time of production to the time of use. Because the particles once dried become aggregated particles, and are hardly re-dispersed even in water. The concentration of solid contents is preferably 1 to 50% by mass, and more preferably 5 to 35% by mass. The dispersing medium is preferably water, but if necessary, a water-soluble solvent (alcohols such as methanol, ethanol and the like, ketones such as acetone and the like, esters such as ethyl acetate and the like) by 70% by mass or less based on water may be used in combination. As the mixing method, a method of mixing the water-solublizing state substance of (B) with the dry powdery particles of (A), or a method of adding the water-solublizing state substance of (B) to polymerized (A) before drying followed by mixing and then drying with heat may be mentioned, but the former is preferable. When the mixing is carried out using the second crosslinking agent, a method of simultaneously mixing the dry powdery particles of (A), the water-solublizing state substance of (B) and the second crosslinking agent followed by drying with heat wherein (A) is obtained by aqueous solution polymerization between a water-soluble monomer and the first crosslinking agent, or a method of mixing the water-solublizing state substance of (B) after the dry powdery particles of (A) and the second crosslinking agent are mixed and dried with heat can be mentioned, but the latter is preferable.

Further, the water content in a mixture of the water-containing gel of (A) and (B) mentioned in the above method (i) is not specifically limited, but is preferably 2 to 10-fold based on the solid contents of (A). When it is 2-fold or more, the uniformity at kneading is great, and the improvement effect of the diffusion and absorption speed of the absorbents obtained is good. When 10-fold or less, it is economical because the drying time is short.

As the mixing equipment for compounding and homogeneously mixing (B) with (A) in a water-containing gel, conventionally known equipment can be used. As the example of the specific equipment, a double arm type kneader, internal mixer (Banbury mixer), self cleaning type mixer, gear compounder, screw type extruder, screw type kneader and a mincing machine and the like can be mentioned. The combination of a plural number of the equipment can also be used.

The drying temperature of the water-containing gel state mixture to which (B) has been added is usually 60 to 230° C., preferably 100 to 200° C., and in particular, preferably 105 to 180° C. With a drying temperature of 60° C. or more, it is economical because the drying time is short, and when the temperature is 230° C. or less, a side reaction or the decomposition of the resin and the like do not occur, and also the absorption performance and the diffusion and absorption speed are not lowered.

The equipment which dries a mixture of (B) and (A) in a water-containing gel state may be common equipment, and for example, a drum dryer, concurrent band dryer (tunnel dryer), ventilated band dryer, spouting stream (nozzle jet) dryer, box type hot air dryer, infrared dryer, and the like can be mentioned. The heat source is not specifically limited. The combination of a plural number of these dryers can be also used.

As an additive or an extending agent, a residual monomer reducing agent (for example, sodium sulfite, hydrogen peroxide and the like), surfactant, antibiotic (for example, a quaternary ammonium salt compound, chlorohexidine compound, metal salt-based antibiotic and the like), antiseptic, aromatizer, deodorant, colorant, antioxidant, and fine filler other than (B), and the like can be added in the mixture of (A) and (B) of the present invention if necessary. The addition amount is preferably 0.1 to 50% by mass based on (A) plus (B). These additives can be added during the drying or also after drying of the water-containing gel state mixture.

As a surfactant, there can be mentioned is an anion activator, nonionic activator, cation activator, amphoteric activator, and for example, a surfactant described in the specification of U.S. Pat. No. 4,331,447. One or 2 or more of these may be used in combination.

Examples of anionic surfactants include hydrocarbon series ether carboxylic acid having the carbon number of 8 to 24 or salts thereof [oxyethlene (polymerization degree=1 to 100) lauryl ether acetate sodium, oxyethlene (polymerization degree=1 to 100) lauryl sulfosuccinate disodium etc.], hydrocarbon series sulfate ester salts having the carbon number of 8 to 24 [sodium lauryl sulfate, oxyethlene (polymerization degree=1 to 100) lauryl sulfate sodium, oxyethlene (polymerization degree=1 to 100) lauryl sulfate triethanolamine, oxyethlene (polymerization degree=1 to 100) coconut oil fatty acid monoethanolamide sulfate sodium], hydrocarbon series sulfonate salts having the carbon number of 8 to 24 [sodium dodecylbenzenesulfonate etc.], hydrocarbon series phosphate salts having the carbon number of 8 to 24 [sodium laurylphosphate, oxyethlene (polymerization degree=1 to 100) lauryl ether phosphate sodium etc.], fatty acid salts [sodium laurate, lauric acid triethanolamine etc.], acylated amino acid salts [coconut oil fatty acid methyl taurine sodium, coconut oil fatty acid sarcosine sodium, coconut oil fatty acid sarcosine triethanolamine, N-coconut oil fatty acid acyl-L-glutamic acid triethanolamine, N-coconut oil fatty acid acyl-L-glutamate sodium, lauroylmethyl-β-alanine sodium etc.], and others [sulfosuccinic acid oxyethlene (polymerization degree=1 to 100) lauroylethanolamide disodium etc.].

Examples of the nonionic surfactants include fatty acid series alcohols (carbon number of 8 to 24) alkyleneoxide (carbon number of 2 to 8) adduct (polymerization degree=1 to 100) [lauryl alcohol ethylene oxide adduct (polymerization degree=20), oleyl alcohol ethylene oxide adduct (polymerization degree=10), sperm alcohol ethylene oxide adduct (polymerization degree=35) etc.], oxyalkylene (carbon number of 2 to 8, polymerization degree=1 to 100) higher fatty acid (carbon number of 8 to 24) ester [monostearic acid polyethylene glycol (polymerization degree=20), distearic acid polyethylene glycol (polymerization degree=30) etc.], polyhydric (2-hydric to 10-hydric or more-hydric) alcohol fatty acid (carbon number of 8 to 24) ester [monostearic acid glycerin, monostearic acid ethylene glycol, sorbitan lauric acid (mono/di) ester, sorbitan palmitic acid (mono/di) ester, sorbitan stearic acid (mono/di) ester, sorbitan oleic acid (mono/di) ester, sorbitan coconut oil (mono/di) ester stc.], polyoxyalkylene (carbon number of 2 to 8, polymerization degree=1 to 100) polyhydric (2-hydric to 10-hydric or more-hydric) alcohol higher fatty acid (carbon number of 8 to 24) ester [polyoxyethylene (polymerization degree=10) sorbitan lauric acid (mono/di) ester, polyoxyethylene (polymerization degree=20) sorbitan palmitic acid (mono/di) ester, polyoxyethylene (polymerization degree=15) sorbitan stearic acid (mono/di) ester, polyoxyethylene (polymerization degree=10) sorbitan oleic acid (mono/di) ester, polyoxyethylene (polymerization degree=25) lauric acid (mono/di) ester, polyoxyethylene (polymerization degree=50) stearic acid (mono/di) ester, polyoxyethylene (polymerization degree=18) oleic acid (mono/di) ester, sorbitan, polyoxyethylene (polymerization degree=50) dioleic acid methyl glucoside etc.], fatty acid alkanolamide [1:1 type coconut oil fatty acid diethanolamide, 1:1 type luric acid diethanolamide etc.], polyoxyalkylene (carbon number of 2 to 8, polymerization degree=1 to 100) alkyl (carbon number of 1 to 22) phenylether(polyoxyethylene(polymerization degree=20) nonilphenylether etc.), polyoxyalkylene (carbon number of 2 to 8, polymerization degree=1 to 100) alkyl (carbon number of 8 to 24) aminoether and alkyl (carbon number of 8 to 24) dialkyl (carbon number of 1 to 6) amineoxide [lauryldimethylamineoxide etc.], polydimethylsiloxane ethyleneoxide adduct, polyoxyethylene polyoxypropylene block polymer (weight average molecular weight=150 to 10,000) and the like.

Examples of the cationic surfactants include quaternary ammonium salt type [stearyltrimethylammonium chloride, behenyltrimethylammonium chloride, distearyldimethylammonium chloride, ethyl sulfate lanolin fatty acid aminopropylethyldimethylammonium etc.], amine salt type [stearic diethylaminoethylamide lactate, dilaurylamine hydrochloride, oleylamine lactate etc.], and the like.

Examples of the amphoteric surfactants include betaine type amphoteric surfactants [coconut oil fatty acid amidopropyldimethylaminoacetic acid betaine, lauryldimethylaminoacetic acid betaine, 2-alkyl-N-carboxymethyl-N-hydroxyethylimidazolinium betaine, laurylhydroxysulfo betaine, lauroylamidoethylhydroxyethylcarboxymethyl betaine hydroxypropylphosphate sodium etc.], amino acid type amphoteric surfactants [β-laurylaminopropionate sodium etc.], and the like.

Examples of the antioxident include hindered phenol series antioxident such as triethyleneglycol-bis-[3-(3-t-butyl-5-methyl-4-hydroxyphenyl)propionate], 1,6-hexanediol-bis[3-(3,5-di-t-butyl-4-hydroxyphenyl)propionate], octadecyl-3-(3,5-di-t-butyl-4-hydroxyphenylpropionate, 3,5-di-t-butyl-4-hydroxybenzylphosphonate-diethyl ester and the like; amine series antioxidants such as n-butylamine, triethylamine, diethylaminomethyl methacrylate and the like, a combination of 2 or more of them.

Examples of the ultraviolet absorbing agent include benzotriazole series ultraviolet absorbing agents such as 2-(5-methyl-2-hydroxyphenyl)benzotriazole, 2-(3,5-di-t-butyl-2-hydroxyphenyl)benzotriazole, 2-(3,5-di-t-butyl-2-hydroxyphenyl)-5-chlorobenzotriazole, 2-(3,5-di-t-amyl-2-hydroxypehnyl)benzotriazole and the like; triazine series ultraviolet absorbing agents such as 2-(4,6-diphenyl-1,3,5-triazin-2-yl)-5-[(hexyl)oxy)-phenol and the like; benzophenone series ultraviolet absorbing agents such as 2-hydroxy-4-n-octyloxybenzophenone and the like; oxalic acid anilide series ultraviolet absorbing agents such as 2-ethoxy-2'-ethyloxalic acid bisanilide and the like, and a combination of 2 or more of them.

Examples of the inorganic powder include calcium carbonate, kaolin, talc, mica, bentonite, clay, sericite, asbestos, glass fiber, carbon fiber, glass powder, glass baloon, sand bar baloon, coal powder, metal powder, ceramic powder, silica, zeolite, slate powder and the like. The form thereof may be arbitrary and an average particle size is preferably 0.1 micron to 1 mm.

Examples of the pigment include carbon black, titanium oxide, red iron oxide, minium, parared, Prussian blue and the like.

Examples of the organic fibrous material include natural fibers [cellulose sereis (cotton, sawdust, straw etc.) and others, grass coal, wool, microfibril, bacterial cellulose etc.], artificial fibers (cellulose series such as rayon, acetate etc.), synthetic fibers (polyamide, polyester, acryl etc.), pulp [mechanical pulp (ground pulp from log, Asplund method ground pulp etc.), chemical pulp (sulfite pulp, soda pulp, sulfate pulp, nitric acid pulp, chlorine pulp etc.), semichemical pulp, regenerated pulp (for example, materials prepared by mechanically crushing or grinding papers once made from pulps, or regenerated wastepaper pulp prepared by mechanically crushing or grinding wastepapers etc.) and the like.

The absorbents of the present invention, when used for the sanitary goods such as a paper diaper and napkin, is effective for improving a dry feeling and for reducing the leakage, by setting the diffusion and absorption speed to bovine blood (containing 3.8% of citric acid; hematocrit value=20% by volume) as 25 to 65 ml/g and preferably 28 to 60 ml/g. Further, the absorbents of the present invention obtained by surface-crosslinking has an improved initial absorption amount under load, and it is more effective when those absorbents are used for the sanitary goods such as a paper diaper and napkin since the dry feeling may be improved and also the leakage may be lowered by setting the diffusion and absorption speed to bovine blood as 25 to 65 ml/g and preferably 28 to 60 ml/g, and by setting the initial absorption amount under load to bovine blood as 18 to 40 g/g and preferably 25 to 40 g/g. Further, with regard to physiological saline, the absorbents exceed in the diffusion and absorption speed, the initial absorption amount under load and the water retention amount. Still, the hematocrit value of bovine blood used can be adjusted using physiological saline or plasma. Moreover, although the value may be occasionally somewhat different depending on the bovine blood used, the superiority or inferiority of the absorbents can be judged. diffusion and absorption speed, the initial absorption amount under load and the water retention amount. Still, the hematocrit value of bovine blood used can be adjusted using physiological saline or plasma. Moreover, although the value may be occasionally somewhat different depending on the bovine blood used, the superiority or inferiority of the absorbents can be judged.

(Absorbable Constructs and Absorbable Articles)

The absorbents (C) of the present invention is extremely superior in absorption properties such as the diffusion and absorption speed and the absorption amount, and articles with excellent absorption performance can be obtained by applying the absorbents to the various absorbable constructs (F) and absorbable articles.

As the method of applying the absorbent (C) of the present invention to the various absorbable constructs (F), the method below may be mentioned for the manufacture of the absorbable constructs constituted from a matrix of (C) and a fibrous material (E), for example, a method (1) by scattering (C) between layers of fibrous materials consisting of pulp, heat-adherable fibers and so on arranged in layers;
(2) by mixing (C) with fibrous materials consisting of pulp, heat-adherable fibers and so on; or
(3) by sandwiching (C) on demand together with fibrous materials by 2 or more sheets of water-absorbing paper or nonwoven fabric.

As (E), fibrous materials which have been conventionally used for absorbable articles such as, for example, various flap pulp and cotton pulp can be mentioned, and raw materials (coniferous trees, broad-leaved trees, etc.), production processes [chemical pulp, semi chemical pulp, chemi-thermo mechanical pulp polyethylene-based fibers, polypropylene-based fibers), polyester-based fibers (for example, polyethylene terephthalate-based fibers), polyolefin-polyester complexed fibers, polyamide-based fiber, polyacrylonitrile-based fibers and the like may be mentioned.

The length and thickness of (E) are not specifically limited, and usually, the length is preferably in a range of 1 to 200 mm and the thickness is preferably in a range of 0.1 to 100 denier. Also the shape is not specifically limited so far as it is fibrous, and web form, narrow cylindrical form, shredded split yarn, staple form, filament form and the like are exemplified.

The addition amount of the absorbent (C) of the present invention to the absorbable constructs (F) can be variously changed in accordance with the kind and size of the absorbable constructs and the aimed absorption performance, but the amount of (C) is preferably 30 to 95% by weight based on the mass of (F) and more preferably, 40 to 95% by weight.

The absorbable articles of the present invention is preferably an absorbable article provided with said absorbable constructs (F), a liquid-permeable sheet and an air-permeable back sheet, and more preferably, an article as sanitary goods. As the sanitary goods, for example, a paper diaper (paper diaper for children, paper diaper for an adult, and the like), napkin (sanitary napkin and the like), paper towel, pad (pad for incontinence, under pad for operation and the like), pet sheet (urine absorbing sheet for pets) and the like can be mentioned. A napkin and a paper diaper are preferable.

EXAMPLES

The present invention is further illustrated below according to Examples and Comparative Examples, however the present invention is not limited therewith. Further, the diffusion and absorption speed, the initial absorption amount under load, the absorption amount under load and the water retention amount of the obtained absorbents were measured by methods described below. Hereinafter, % indicates % by mass unless otherwise specifically defined.

[Measurement Method of Diffusion and Absorption Speed]

0.10 g of an absorbent adjusted to a grain size of 30 to 60 mesh by a JIS standard sieve is prepared as a sample.

Figure 1:
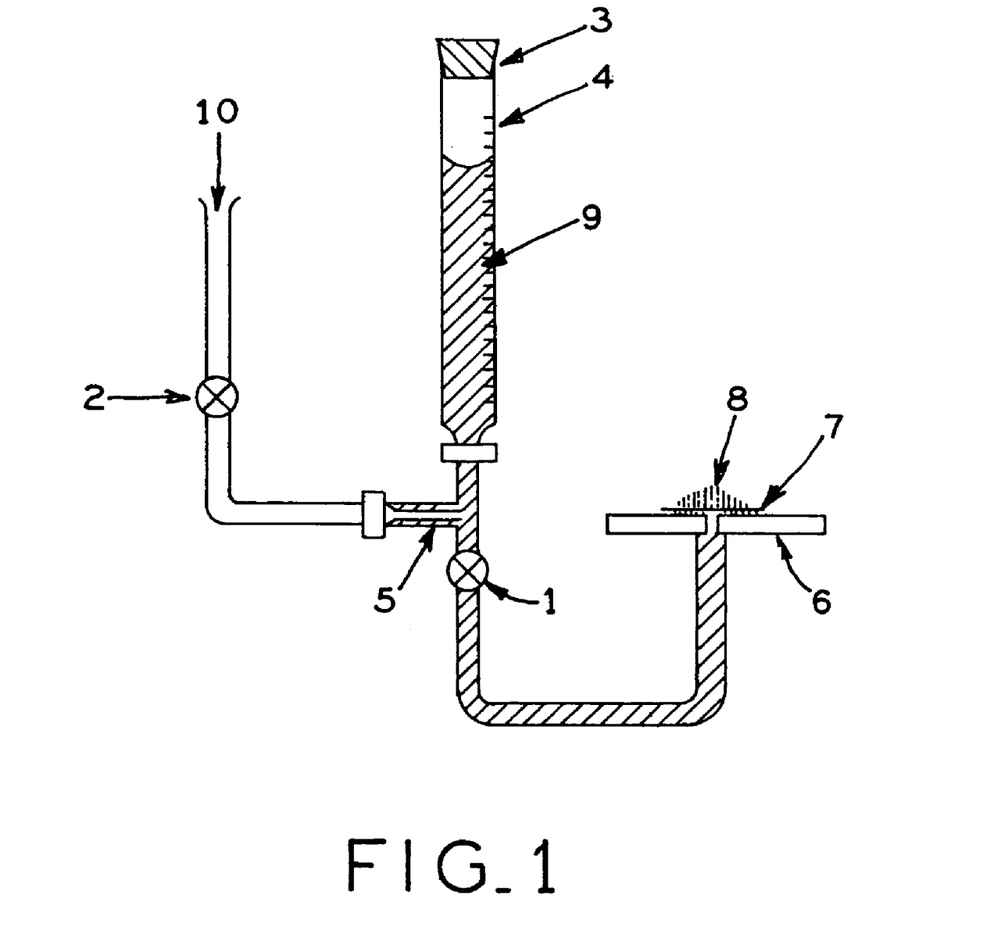
FIG. 1 is a drawing showing a device for measuring the diffusion and absorption speed of the present invention.

The device shown in FIG. 1 is placed on a level stand. Further, it is to be confirmed that the arrangement of the narrow duct 5 which is the inlet of air and that of the upper surface of the flat plate 6 are horizontal.

The cock 1 at the lowest portion of a burette and the cock 2 at a side hole are closed, and bovine blood (containing 3.8% of citric acid; the hematocrit value=20% by volume: manufactured by Towa Pure Chemicals Co.) is charged in the burette 4 from the top of the burette. Then, the uppermost portion of the burette is closed with the rubber stopper 3, and the graduation showing the volume of bovine blood in the burette is read before opening the cock 1 at the lowest portion and the cock 2 at the side hole. The plain cloth nylon mesh 7 (5 cm×5 cm) of 63 μm opening is laid on the flat plate 6 which has a 3 mm pore, and 0.10 g of the sample 8 is placed on it. The absorption starts once the sample is placed, therefore the measurement starts from this point of time, and the amount absorbed after 2 minutes is measured by reading the graduation of the burette. The 10-fold value of the decreased volume of bovine blood in the burette by absorption of the blood is referred to as the diffusion absorption amount.

[Measurement Method of the Initial Absorption Amount Under Load and the Absorption Amount]

0.10 g of the sample of an absorbent adjusted to a grain size of 30 to 60 mesh by a JIS standard sieve is charged and leveled in a cylindrical plastic tube (30 mmφ in inner diameter, 60 mm in height) at which a 250-mesh nylon net was attached to the bottom. A weight having an outer diameter of 30 mmφ is mounted on the absorbent, and thereby a load of 20 g/cm$^2$ is applied. The plastic tube containing the absorbent is quietly placed at the center of a Petri dish (12 cmφ in diameter) containing 60 ml of the bovine blood, with the nylon net side facing downward. The mass of the absorbent increased by absorbing the bovine blood is measured after 10 minutes and 60 minutes. The 10-fold value of the increased weight after 5 minutes is referred to as the initial absorption amount under load to the bovine blood, and the 10-fold value of the increased weight after 60 minutes is referred to as the absorption amount under load to the bovine blood.

[Measurement Method of Blood Retention Amount]

1.00 g of the sample of an absorbent adjusted to a grain size of 30 to 60 mesh by a JIS standard sieve is charged in a tea bag (20 cm in length, 10 cm in width) made by a 250-mesh nylon net. The tea bag is immersed in 500 ml of the bovine blood for 60 minutes for absorption, then hung for 15 minutes to drain water, and further centrifuged for dewatering with a centrifugal force of 150G for 90 seconds by a dewatering centrifuge. The increased mass is measured to obtain the blood retention amount with regard to the bovine blood.

Example 1

Into a 1 L glass reactor, 77 g of sodium acrylate, 22.8 g of acrylic acid, 0.2 g of N,N'-methylenebisacrylamide, 395 g of deionized water and 0.001 g of dichlorotris(triphenylphosphine)ruthenium were charged and the temperature of the content was kept at 3° C. while stirring and mixing.

After the dissolved oxygen amount was decreased to 1 ppm or less by influxing nitrogen into the content, 1 g of a 1% aqueous solution of hydrogen peroxide, 1.2 g of a 0.2% aqueous solution of ascorbic acid and 2.8 g of a 2% aqueous solution of 2,2'-azobisamidinopropane dihydrochloride were added and mixed to initiate polymerization. The polymerizing was continued for about 5 hours to obtain water-containing gel state water-absorbable resin (A1). After (A1) was ground to a size of 2 to 5 mm by an internal mixer, 0.1 g of ethylene glycol diglycidyl ether and 1 g of KLEBOSOL 30H25 (pH for 10% water dispersion liquid=2.5, average particle diameter=25 nm, specific surface area=120 m$^2$/g, solid content 30%) (B1) manufactured by Clariant Japan Co., Ltd. which is the aqueous colloidal solution of nonporous spherical amorphous silicon oxide were added, the mixture was further homogeneously mixed by the internal mixer, and then dried at a condition of 150° C. and an air flow rate of 2.0 m/sec. by a ventilated band drier (manufactured by Inoue Kinzoku Kogyo Co., Ltd.).

The dried product obtained was pulverized and adjusted to a grain size of 20 to 100 mesh to obtain the absorbent (1). The evaluation result of performance of the absorbent (1) is shown in Table 1.

Example 2

After the water-containing gel state absorbable resin (A1) obtained in Example 1 was ground to a size of 2 to 5 mm by an internal mixer, 0.1 g of ethylene glycol diglycidyl ether was added. The mixture was further homogeneously mixed by the internal mixer, and then dried at a condition of 150° C. and an air flow rate of 2.0 m/sec. by a ventilated band drier (manufactured by Inoue Kinzoku Kogyo Co., Ltd.). The dried product obtained was pulverized and adjusted to a grain size of 20 to 100 mesh. Next, 1 g of (B1) was added thereto and after the mixture was further homogeneously mixed by the internal mixer, it was adjusted to a grain size of 20 to 100 mesh to obtain the absorbent (2). The evaluation result of performance of the absorbent (2) is shown in Table 1.

Example 3

After the water-containing gel state absorbable resin (A1) obtained in Example 1 was ground to a size of 2 to 5 mm by an internal mixer, the same amount of (B1) as that in Example 1 was added to be mixed, and then an absorbent having a grain size of 20 to 100 mesh was obtained in a similar manner as in Example 1. 2 g of a water/methanol mixed solution (water/methanol=30/70) containing 1% of ethylene glycol diglycidyl ether was added to 10 g of the absorbent while stirring at high speed, and crosslinked with heat at 140° C. for 30 minutes to obtain the surface-crosslinked type absorbent (3). The evaluation result of performance of the absorbent (3) is shown in Table 1.

Examples 4 and 5

The surface-crosslinking type absorbents (4) and (5) were obtained in the similar manner as in Example 1, except that the additional amount of (B1) in Example 2 was changed 1 g to 0.5 g or 3 g. The evaluation results of performance of these are shown in Table 1.

Examples 6 and 7

The absorbents (6) and (7) were obtained in a similar manner as in Example 2, except that (B1) was replaced by the same amount of the below-mentioned nonporous spherical monoparticles (B2) or (B3) in Example 2. The evaluation results of performance of these absorbents are shown in Table 1.

(B2): KLEBOSOL 30CAL25 (pH for 10% water dispersion liquid=4.0, average particle diameter=25 nm, specific surface area=200 m$^2$/g, solid content of 30%) manufactured by Clariant Japan Co., Ltd.

(B3): KLEBOSOL 30R9 (pH for 10% water dispersion liquid=10.7, average particle diameter=9 nm, specific surface area=300 m$^2$/g, solid content of 30%) manufactured by Clariant Japan Co., Ltd.

Examples 8 and 9

The absorbents (8) and (9) were obtained in a similar manner as in Example 2, except that dichlorotris(triphenylphosphine)ruthenium was replaced by the same amount of chlorotris(triphenylphosphine)rhodium or dichlorotetrakis(triphenylphosphine)ruthenium in Example 2. The evaluation results of performance of these absorbents are shown in Table 1.

Example 10

Into a 1 L glass reactor, 77 g of sodium acrylate, 22.75 g of acrylic acid, 0.25 g of N,N'-methylenebisacrylamide, 329.3 g of deionized water and dichloro(tristriphenylphosphine)ruthenium were charged, 1 g of (B1) was added while stirring and mixing, and the temperature of the content was kept at 3° C.

After the dissolved oxygen amount was decreased to 1 ppm or less by influxing nitrogen into the content, 1 g of a 1% aqueous solution of hydrogen peroxide, 1.2 g of a 0.2% aqueous solution of ascorbic acid and 2.8 g of a 2% aqueous solution of 2,2'-azobisamidinopropane dihydrochloride were added and mixed to initiate polymerization. The polymerizing was continued for about 5 hours to obtain the water-containing gel state absorbable resin (AB1) containing (B1).

After (AB1) was ground to a size of 2 to 5 mm by an internal mixer, it was dried at a condition of 150° C. and an air flow rate of 2.0 m/sec. by a ventilated band drier. The dried product obtained was pulverized and adjusted to have a grain size of 20 to 100 mesh to obtain an absorbent. 2 g of a water/methanol mixed solution (water/methanol=30/70) containing 1% of ethylene glycol diglycidyl ether was added to 100 g of the absorbent while stirring at high speed, and crosslinked with heat at 140° C. for 30 minutes to obtain the absorbent (10). The evaluation result of performance of the absorbent (10) is shown in Table 1.

Example 11

Into a 1 L glass reactor, 81.75 g of acrylic acid, 0.25 g of N,N'-methylenebisacrylamide and 341 g of deionized water were charged, and the temperature of the content was kept at 3° C. while stirring and mixing.

After the dissolved oxygen amount was decreased to 1 ppm or less by influxing nitrogen into the content, 1 g of a 1% aqueous solution of hydrogen peroxide, 1.2 g of a 0.2% aqueous solution of ascorbic acid and 2.8 g of a 2% aqueous solution of 2,2'-azobisamidinopropane dihydrochloride were added and mixed to initiate polymerization. The polymerizing was continued for about 5 hours to obtain acid type water-containing gel state polymer.

The water-containing gel state polymer was ground to a size of 2 to 5 mm by an internal mixer while 109.1 g of a 30% sodium hydroxide aqueous solution was added and kneaded to obtain 72% by mol of the carboxylic acid group neutralized water-containing gel state water-absorbable resin (A2).

After the same amount of (B1) as in Example 1 was added to the water-containing gel state water-absorbable resin (A2) and homogeneously mixed, the mixture was dried at a condition of 150° C. and an air flow rate of 2.0 m/sec. by a ventilated band drier.

The dried product obtained was pulverized and adjusted to a grain size of 20 to 100 mesh to obtain an absorbent. 2 g of a water/methanol mixed solution (water/methanol=30/70) containing 1% of ethylene glycol diglycidyl ether was added to 100 g of the absorbent while stirring at high speed, and crosslinked with heat at 140° C. for 30 minutes to obtain the absorbent (11). The evaluation result of performance of the absorbent (11) is shown in Table 1.

Comparative Example 1

After the water-containing gel state water-absorbable resin (A1) obtained in Example 1 was ground to a size of 2 to 5 mm by an internal mixer, 0.1 g of ethylene glycol diglycidyl ether was added, the mixture was further homogeneously mixed by the internal mixer, and then dried at a condition of 150° C. and an air flow rate of 2.0 m/sec. by a ventilated band drier.

The dried product obtained was pulverized and adjusted to a grain size of 20 to 100 mesh to obtain a comparative absorbent (a). The evaluation result of performance of the comparative absorbent (a) is shown in Table 1.

Comparative Example 2

After the water-containing gel state water-absorbable resin (A1) obtained in Example 1 was ground to a size of 2 to 5 mm by an internal mixer, it was dried at a condition of 150° C. and an air flow rate of 2.0 m/sec. by a ventilated band drier. The dried product obtained was pulverized and adjusted to a grain size of 20 to 100 mesh to obtain an absorbent. 2 g of a water/methanol mixed solution (water/methanol=30/70) containing 10% of ethylene glycol diglycidyl ether was added to 100 g of the absorbent while stirring at high speed, and crosslinked with heat at 140° C. for 30 minutes to obtain the surface-crosslinked type comparative absorbent (b). The evaluation result of performance of the comparative absorbent (b) is shown in Table 1.

Comparative Example 3

After the water-containing gel state water-absorbable resin (A1) obtained in Example 1 was ground to a size of 2 to 5 mm by an internal mixer, 0.1 g of ethylene glycol diglycidyl ether and 10 g of a 3% water dispersion liquid of AEROSIL200 (average particle diameter=220 nm, primary particle diameter=12 nm, specific surface area=200 m$^2$/g) (comparative B1) manufactured by Nippon AEROSIL K.K. were added, the mixture was further homogeneously mixed by the internal mixer, and then dried at a condition of 150° C. and an air flow rate of 2.0 m/sec. by a ventilated band drier. The dried products obtained were pulverized and adjusted to a grain size of 20 to 100 mesh to obtain an absorbent. 2 g of a water/methanol mixed solution (water/methanol=30/70) containing 1% of ethylene glycol diglycidyl ether was added to 100 g of the absorbent while stirring at high speed, and crosslinked with heat at 140° C. for 30 minutes to obtain the surface-crosslinked type absorbent (c). The evaluation result of performance of the absorbent (c) is shown in Table 1.

Comparative Example 4

After the water-containing gel state water-absorbable resin (A1) obtained in Example 1 was ground to a size of 2 to 5 mm by an internal mixer, 0.1 g of ethylene glycol diglycidyl ether was added, the mixture was further homogeneously mixed by the internal mixer, and then dried at a condition of 150° C. and an air flow rate of 2.0 m/sec. by a ventilated band drier (manufactured by Inoue Kinzoku Kogyo Co., Ltd.). Then, 0.3 g of (comparative B1) was added, the resulting mixture was further homogeneously mixed by the internal mixer, and adjusted to a grain size of 20 to 100 to obtain the absorbent (d). The evaluation result of performance of the absorbent (d) is shown in Table 1.

The results are shown in Table 1.

TABLE 1

| Absorbent | | Diffusion and absorption speed (ml/g) | Initial absorption amount under load (g/g) | absorption amount under load (g/g) | Blood retention amount (g/g) |
|---|---|---|---|---|---|
| Example 1 | (1) | 29 | 24 | 32 | 44 |
| Example 2 | (2) | 31 | 26 | 34 | 46 |
| Example 3 | (3) | 29 | 24 | 32 | 40 |
| Example 4 | (4) | 30 | 25 | 33 | 45 |
| Example 5 | (5) | 32 | 27 | 35 | 47 |
| Example 6 | (6) | 32 | 26 | 34 | 47 |
| Example 7 | (7) | 30 | 26 | 33 | 45 |
| Example 8 | (8) | 29 | 24 | 33 | 42 |
| Example 9 | (9) | 29 | 24 | 32 | 41 |
| Example 10 | (10) | 29 | 23 | 32 | 40 |
| Example 11 | (11) | 29 | 24 | 32 | 40 |
| Comparative Example 1 | (a) | 24 | 17 | 27 | 30 |
| Comparative Example 2 | (b) | 22 | 17 | 29 | 34 |
| Comparative Example 3 | (c) | 25 | 20 | 30 | 36 |
| Comparative Example 4 | (d) | 23 | 17 | 28 | 36 |

INDUSTRIAL APPLICABILITY

The absorbents of the present invention exhibit effect shown below even in a liquid to be absorbed containing water-insoluble or hardly water-soluble matters such as menstrual blood or feces.
1) Thanks to the fast diffusion and absorption speed and good initial absorption amount under load (representing absorption speed when load is applied), the advantages in the improvement of initial dry feeling and the decrease in leaking are obtained when used as absorbents, for example, sanitary goods.
2) The water/blood retention amount and in the absorption amount under load is also superior.
3) Since they are the water-insoluble nonporous spherical monoparticles having an average particle diameter of 1 to 50 nm, they are excellent in handling property of powder. Moreover, like the granulated fine particles, they hardly generate fine particles caused by the destruction of the absorbent particle with the mechanical shearing force or friction.

4) Since the water-insoluble nonporous spherical monoparticles having an average particle diameter of 1 to 50 nm, when they are formed into absorbents by mixing with fibrous materials such as pulp, they hardly fall from fibrous materials even if an external force such as vibration is added.

5) Unlike the improvement by a pyrolytic foaming agent, the deterioration of performance does not occur during a production process because radicals and such are not generated when they are dried with heat. Therefore, absorbents not only having an excellent diffusion and absorption speed and the absorption performance, but also only having small amount of water-soluble components are obtained.

6) The improvement of the diffusion and absorption speed can be designed by a simple method of mixing nonporous spherical monoparticles during the step of polymerizing the water-absorbable resin or at any step from after polymerization to after drying.

The use of the absorbable articles of the present invention is preferably the above sanitary goods. Further, it is useful not only for sanitary goods, but also for various uses such as an urine gelling agent of a portable toilet, freshness preserver of greengrocery, drip absorbent for such as meat, fish and shellfish, a cooling agent, disposable body warmer, gelling agent for cells, water retention agent for such as plants and soil, dew inhibitor, sealant, packing materials, and artificial snow.

The description of codes is as described below.
1. Cock
2. Cock
3. Rubber stopper
4. Burette
5. Narrow duct
6. Flat plate having a pore
7. Nylon mesh
8. Sample
9. Bovine blood
10. Atmospheric pressure

What is claimed is:

1. A process for producing an absorbent (C), comprising the steps of:
   (1) carrying out polymerization in the presence of a complex compound (d) of a metal element (d1) and ligand (d2) in which the ligand is an anion or a neutral molecule to obtain a water absorbable resin (A); and
   (2) mixing a water-insoluble nonporous spherical monoparticle (B) having an average particle diameter of 1 to 50 nm in the water-solubilized state with said resin (A) in dry form, or admixing said (B) with said resin (A) before drying and then drying the mixture under heating.

2. The process of claim 1, wherein said (B) is water-insoluble nonporous spherical monoparticle in the water-solublizing state.

3. The process of claim 1, wherein the specific surface area of said (B) is 50 to 400 m²/g.

4. The process of claim 1, wherein said (B) is an inorganic water-insoluble nonporous spherical monoparticle.

5. The process of claim 4, wherein said (B) is amorphous silicon oxide.

6. The process of claim 1, wherein said (A) is a water-absorbable resin obtained by polymerizing a water-soluble monomer and a first crosslinking agent in an aqueous solution.

7. The process of claim 1, wherein said metal element (d1) is a metal element selected from the VIII Group of the $4^{th}$ to $6^{th}$ period and IB Group in the Periodic Table of the long period.

8. The process of claim 1, wherein said ligand (d2) of an anion or a neutral molecule is one or two or more of the ligand selected from a group consisting of the below-mentioned (1) through (3);
   (1) the anion of an atom selected from hydrogen and halogen
   (2) a compound having one or two or more of atoms selected from nitrogen, oxygen, phosphorous and sulfur,
   (3) a conjugated compound.

9. The process of claim 1, wherein said metal element (d1) is selected from the VIII Group of the $5^{th}$ period and said ligand (d2) of an anion or a neutral molecule is a halogen ion and/or a tertiary phosphine compound.

10. The process of claim 1, wherein the amount of said (B) to (A) is 0.01 to 5% by mass.

11. The process of claim 1, wherein the average particle diameter of said (B) is 10 to 30 nm.

12. The process of claim 6, wherein said (A) is obtained by polymerizing a water-soluble monomer and a first crosslinking agent in an aqueous solution, and is further surface-crosslinked by a second crosslinking agent.

13. The process of claim 12, wherein said (A) is a water-absorbable resin obtained by polymerization in the presence of a complex compound (d) of a metal element (d1) and the ligand (d2) of an anion or a neutral molecule, and said (B) is amorphous silicon oxide.

14. A process of producing the absorbent (C) according to claim 1, wherein the water-solublizing state substance of water-insoluble nonporous spherical monoparticle (B) having an average particle diameter of 1 to 50 nm and the second crosslinking agent are simultaneously mixed with the dry powdery particle of said (A) obtained by aqueous solution polymerization between the water-soluble monomer and the first crosslinking, and then the mixture is dried with heat, or wherein the dry powdery particles of said (A) and the second crosslinking agent are mixed and dried with heat, and then the water-solublizing state substance of (B) is mixed.

15. A process for producing an absorbable construct (F), comprising the steps of:
   (1) carrying out polymerization in the presence of a complex compound (d) of a metal element (d1) and ligand (d2) in which the ligand is an anion or a neutral molecule to obtain a water absorbable resin (A);
   (2) mixing a water-insoluble nonporous spherical monoparticle (B) having an average particle diameter of 1 to 50 nm in the water-solubilized state with said resin (A) in dry form, or admixing said (B) with said resin (A) before drying and then drying the mixture under heating to produce an absorbent (C); and (3) manufacturing the absorbable construct (F) composed of a matrix of the absorbent (C) and a fibrous material (E), wherein the absorbent (C) is present in an amount of 30 to 95% by weight based on the absorbable construct (F).

16. A process for producing an absorbable article (G), comprising the steps of:
(1) carrying out polymerization in the presence of a complex compound (d) of a metal element (d1) and ligand (d2) in which the ligand is an anion or a neutral molecule to obtain a water absorbable resin (A);
(2) mixing a water-insoluble nonporous spherical monoparticle (B) having an average particle diameter of 1 to 50 nm in the water-solubilized state with said resin (A) in dry form, or admixing said (B) with said resin (A) before drying and then drying the mixture under heating to produce an absorbent (C);
(3) manufacturing the absorbable construct (F) composed of a matrix of the absorbent (C) and a fibrous material (E), wherein the absorbent (C) is present in an amount of 30 to 95% by weight based on the absorbable construct (F); and
(4) preparing the absorbable article (G) provided with the absorbable construct (F), a liquid-permeable sheet and an air-permeable back sheet.

17. The process of claim 16, the absorbable article (G) being sanitary goods comprising a paper diaper, napkin, pad, paper towel or pet sheet.

* * * * *